United States Patent [19]

Sasa

[11] Patent Number: 4,537,209
[45] Date of Patent: Aug. 27, 1985

[54] DEVICE FOR CLEANING ENDOSCOPES

[75] Inventor: Hiroyuki Sasa, Tokyo, Japan

[73] Assignee: Olympus Optical Co., Ltd., Tokyo, Japan

[21] Appl. No.: 541,423

[22] Filed: Oct. 13, 1983

[30] Foreign Application Priority Data

Oct. 15, 1982 [JP] Japan ................. 57-180827

[51] Int. Cl.³ .............................................. B08B 9/02
[52] U.S. Cl. ................. 134/166 C; 134/102; 128/4
[58] Field of Search ............... 134/166 C, 102; 128/4, 128/6

[56] References Cited

U.S. PATENT DOCUMENTS 4,325,362  4/1982  Ouchi et al. ............................ 128/4

FOREIGN PATENT DOCUMENTS

55394  11/1981  European Pat. Off. ............... 128/4
55-16550  9/1981  Japan .

Primary Examiner—Charles E. Phillips
Assistant Examiner—Renee S. Kidorf

[57] ABSTRACT

A device for cleaning an endoscope includes a communication member which is inserted into an air and water supply cylinder of the endoscope after removing a changeover piston from the cylinder. The communication member is movable between first and second positions and has a through-hole. Through the through-hole, the upper side portion of a water supply passage is communicated with the lower side portion of an air supply passage when the communication member is in the first position, and the upper side portion of the air supply passage is communicated with the lower side portion of the air supply passage when the communication member is in the second position.

6 Claims, 8 Drawing Figures

DEVICE FOR CLEANING ENDOSCOPES

BACKGROUND OF THE INVENTION

The present invention relates to a device for cleaning a passage or passages housed in the endoscope.

The endoscope houses various kinds of passages intended to be selectively used for air supply, water supply, suction and so on. When cleaned after use, therefore, the endoscope needs to be cleaned in these housed passages as well as its outer surface. However, the conventional manner of cleaning these passages comprises connecting the cleaning liquid supply tube to a cap on one end of each of the passages operating the control valve of the endoscope to select the intended passage, and supplying into the passage from the side of its capped end cleaning liquid pressurized by the exclusive pump. On cleaning the endoscope, however, a further extremely troublesome process was needed to detach the endoscope from its light source means, connect the water supply tank and the suction pump to the endoscope, and operate the switch valve. Furthermore, specified means such as the exclusive pump were needed.

SUMMARY OF THE INVENTION

The object of the present invention is to provide a device for cleaning endoscopes wherein the usual water supply means necessarily combined with the endoscope can be used and cleaning liquid supplied from this water supply means is fed into an air supply or water supply passage in the insert section of the endoscope to allow the passage to be easily cleaned.

DETAILED DESCRIPTION OF THE PREFERRED EMBODIMENTS

A cleaning device embodied according to the present invention will be described referring to the accompanying drawings.

A typical example of an endoscope to which the cleaning devices are applied will be described at first referring to FIGS. 1 and 2.

Figure 1:
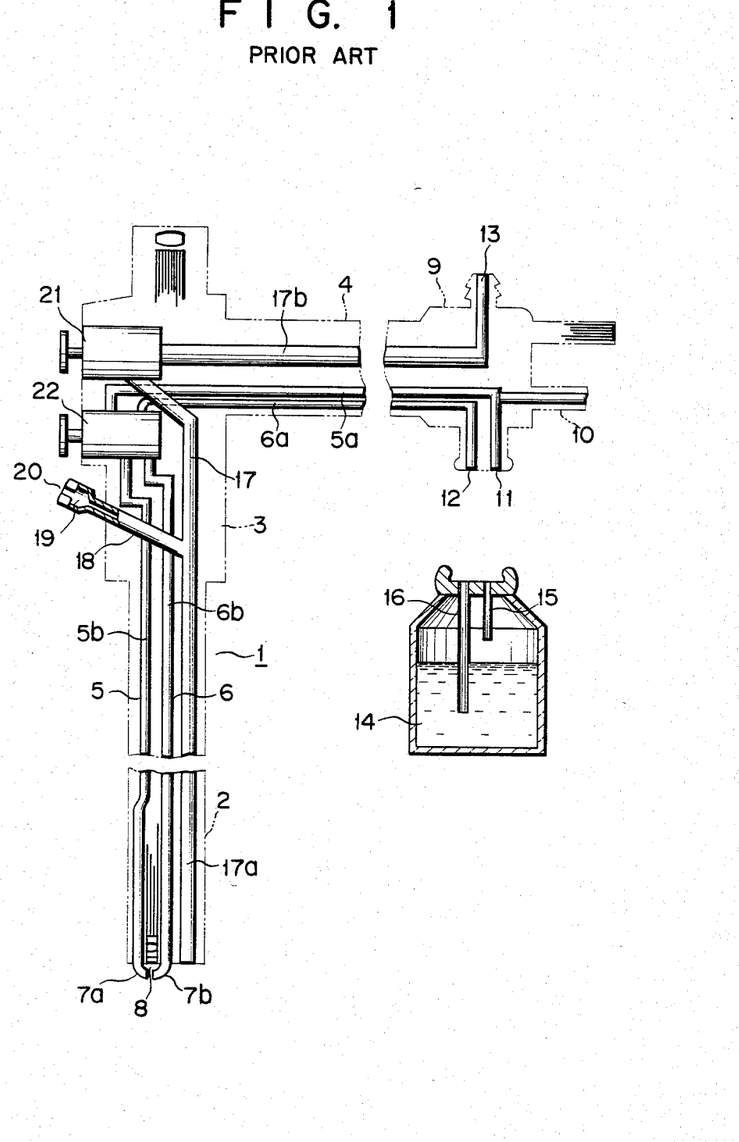
FIG. 1 is a schematical sketch showing the endoscope to which a first embodiment of the present invention is applied.

In FIGS. 1, numeral 1 represents an endoscope, which comprises an insert section 2, an operation section 3 and a light guide cable 4. Various kinds of passages are housed inside the endoscope 1. Air and water supply passages 5 and 6 are arranged throughout the insert and operation sections 2, 3 and the light guide cable 4. These air and water supply passages 5 and 6 are tubes made of synthetic resin, for example. Front ends of the air and water supply passages 5 and 6 are communicated with air and water supply nozzles 7a and 7b arranged at the front end of the insert section 2 of the endoscope 1.

The nozzles 7a and 7b are directed to the outer surface of an observation window 8 to blow cleaning water or air thereonto. To the extended front end of the light guide cable 4 is attached a connector 9, which is provided with first and second air supply caps 10 and 11 to be communicated with the air supply passage 5, and with a water supply cap 12 to be communicated with the water supply passage 6, and with a suction cap 13 to be communicated with a suction passage which will be described later. The first air supply cap 10 is connected to an air supply pump in a light source means (not shown) when the connector 9 is attached to the light source means. The second air supply cap 11 and the water supply cap 12 are connected to their respective air and water supply tubes 15 and 16 arranged in a water supply tank 14. The suction cap 13 is connected to a suction means (which is not shown but comprises the well-known vacuum pump).

A suction passage 17 which is a tube made of synthetic resin, for example, is housed in the endoscope 1 extending through the insert section 2, operation section 3 and light guide cable 4. At the front end side of the endoscope 1, the suction passage 17 is combined with a channel 18 through which an instrument such as a forceps is inserted. The front end of the instrument inserting channel 18 is opened at the front end face of the insert section 2 of the endoscope 1 while the base end thereof is communicated with an insert opening 19 opened outside in the insert section 3. A forceps or instrument holder 20 is freely detachably arranged in the insert opening 19. The instrument inserting channel 18 forms an upper side portion 17a of the suction passage 17, as described above. A control valve 21 is arranged halfway of a lower side portion 17b of the suction passage 17. Another control valve 22 is arranged halfway of the air and water supply passages 5 and 6, which are divided into upper and lower side portions 5a, 6a and 5b, 6b by the control valve 22. The control valves 21 and 22 are arranged, relatively adjacent to each other, on the side of a side face of the operation section 3, as shown in FIG. 1, and have such arrangements as shown in FIG. 2.

The control valve 22 comprises a cylinder 30 and a piston 31. The lower end of the cylinder 30 is closed by a bottom cap 32 to form a bottomed cylinder, and a male screw portion 33 which is smaller in diameter as compared with the other portion of the cylinder 30 is formed around the upper outer circumference of the cylinder 30. A ring-shaped fitting 34 is screwed onto the small-diameter male screw portion 33. The fitting 34 is fitted into a hole 36 formed in a wall 35 of the operation section 3. That portion of the fitting 34 which projects from the hole 36 outside the operation section 3 is formed to have a large diameter portion where a step 37 is formed. The step 37 is contacted with the outer surface of the wall 35. The cylinder 30 is provided at the upper portion thereof with a flange 38 which contacts the inner surface of the wall 35. The wall 35 is thus sandwiched between the flange 38 and the step 37 to hold and fix the cylinder 30 to the wall 35. A fitting flange 39 projects radially from the outermost end of the fitting 34, and an urging member 41 which will be described later is fitted onto the fitting flange 39 to close the cylinder 30, which comprises a large diameter cylindrical portion 42 located on the opening side thereof, and a small diameter cylindrical portion 43 located on the bottom cap side thereof. A taper portion 44 is formed between the large- and small-diameter cylindrical portions 42 and 43. A ring-shaped escape groove 45 is formed on the inner wall of the small diameter cylindrical portion 43 adjacent to the base cap 32. The upper side portion 5a of the air supply passage 5 is communicated with the small diameter cylindrical portion 43 through the wall at the upper side thereof, while the lower side portion 5b of the air supply passage 5 is communicated with the large diameter cylindrical portion 42 through the wall. The upper side portion 6a of the water supply passage 6 is communicated with the small diameter cylindrical portion 43 through the wall located nearer to the bottom cap 32 then the upper side portion 5a of the air supply passage 5 is. The lower side portion 6b of the water supply passage 6 is communicated with the cylinder 30 through the wall located corresponding to the escape groove 45.

The piston 31 is inserted into the cylinder 30 thus constructed. The piston 31 comprises a large diameter rod portion 46 corresponding to the large diameter cylindrical portion 42 of the cylinder 30, a small diameter rod portion 47 corresponding to the small diameter cylindrical portion 43 thereof, and an operating rod portion 48 projected outside the cylinder 30, said large- and small-diameter rod portions 46, 47 and said operating rod portion 48 being coaxially formed integral to one another, and said operating rod portion 48 having a finger push 49 formed as the outer end face thereof. At the end face of the finger push 49 a leak hole 51 opens and extends along the axial direction of the piston 31 through the whole of the large diameter and operating rod portions 46, 48 and through a part of the small diameter rod portion 47. The piston 31 is urged to project outside the cylinder 30 by the urging member 41 which is made by molding an elastic material such as rubber to provide flexibility. The urging member 41 becomes larger in diameter as it comes nearer to its lower end, and it is of skirt shape having a neck portion 52 projected inwardly halfway of its circumferential wall. A ring-shaped groove formed on the inner surface of the lower end of the urging member 41 is fitted onto the fitting flange 39 of the fitting 34, while the upper end of the urging member 41 is engaged with an engaging portion 53 formed just under the finger push 49. When the finger push 49 is pushed by a finger to force the piston 31 into the cylinder 30, starting from the state under which the piston 31 is ready for operation as shown in FIG. 2, the neck portion 52 is elastically deformed, bending inward, to force the piston 31 into the cylinder 30 against the urging force of the urging member 41. A receiving groove 54 which is defined by the flange which is used as the finger push 49 of the piston 31 and by a projection which will be described later is formed around the outer circumference of the operating rod portion 48 of the piston 31, corresponding to the neck portion 52, and when the neck portion 52 is bent inward, this bent part of the neck portion 52 is forced into the receiving groove 54 to thereby prevent the urging member 41 from being deformed to project outward.

The ring-shaped projection 56 is formed around the outer circumference of upper end of the large diameter rod portion 46 of the piston 31 in such a way that the outer circumference of the projection 56 is slidably contacted with the inner face of the large diameter cylindrical portion 42 of the cylinder 30. The upper end face of the projection 56 hits against a stopper 57 which projects inward from the inner face of lower end of the urging member 41, thus stopping the piston 31 from coming out of the cylinder 30 and also defining the upward movement of the piston 31 to keep it ready for operation. A ring-shaped groove 58 is formed around the piston 31 between the large and small diameter rod portions 46 and 47 thereof, and a valve 59 made of elastic material and formed like a ring whose thickness becomes smaller as its outer circumference comes nearer is calked into the groove 58. The outer circumference of the valve 59 slides on the inner face of the large diameter cylindrical portion 42 of the cylinder 30 when the piston 31 reciprocates inside the cylinder 30.

A cylindrical sealing member 61 is fitted onto the small diameter rod portion 47 of the piston 31 and its ring-shaped porjections formed at its both ends slide on the inner face of the small diameter cylindrical portion 43 of the cylinder 30. A ring-shaped communication groove 62 is formed around the outer circumference of the sealing member 61 between both projections thereof, and a ring-shaped path 63 is thus formed between the groove 62 and the inner wall of the small diameter cylindrical portion 43. The small diameter rod portion 47 is provided with a first traverse communication hole 64 for communicating the leak hole 51 with the inside of the large diameter cylindrical portion 42, and with a second traverse communication hole 65 for communicating the leak hole 51 with the upper side portion 5a of the air supply passage 5, when the piston 31 is kept ready for operation as shown in FIG. 2.

Figure 2:
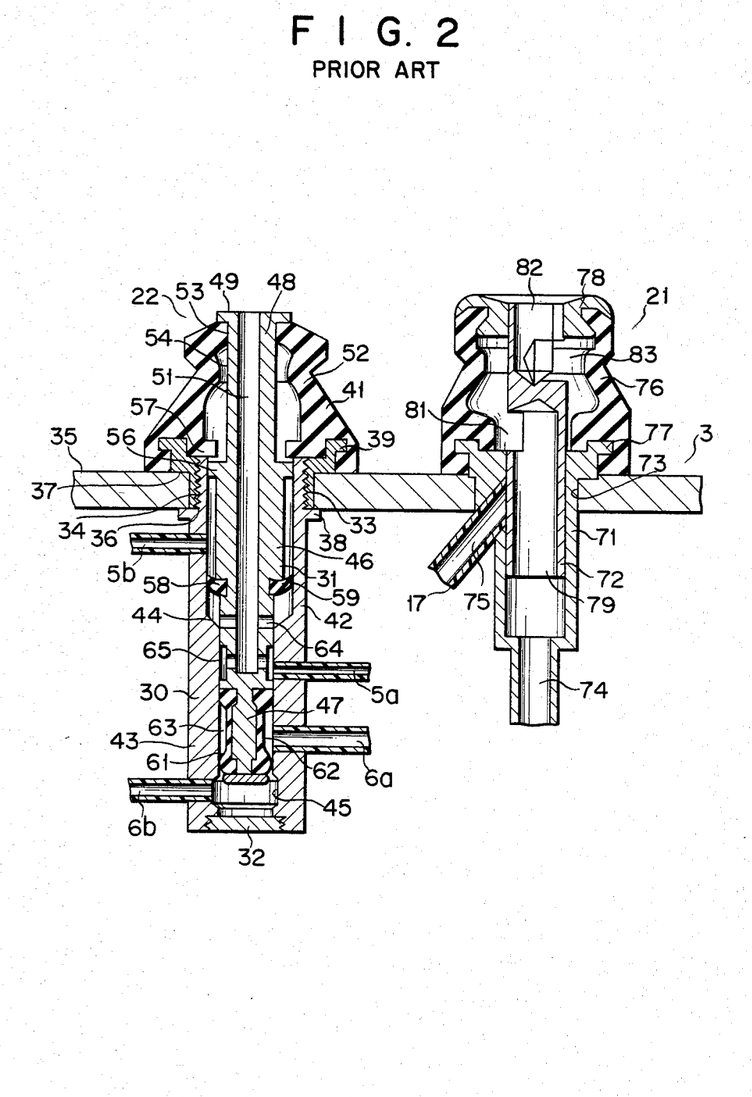
FIG. 2 is a sectional view showing control valves in the endoscope.

In the case of a state under which the control valve 22 for air and water supply is kept unoperative as shown in FIG. 2, air is fed into the leak hole 51 through the upper side portion 5a of the air supply passage 5 and the second communication hole 65. This air is discharged outside through the upper end opening of the leak hole 51. The first communication hole 64 is shut off from the lower side portion 5b by the valve body 59. When air is to be supplied, a finger is put on the finger push 49 of the piston 31 to close the leak hole 51. Air which is being discharged through the leak hole 51 is thus passed through the second communication hole 65, leak hole 51 and first communication hole 64 to push the valve body 59 open and flows into the lower side portion 5b of the air supply passage 5 to be jetted out of the nozzle 7. When water is to be supplied, the piston 31 is pushed into the cylinder 30 against the urging force of the urging member 41, with the opening of the leak hole 51 closed by a finger, so that the valve body 59 is forced onto the taper portion 44 to shield the lower side portion 5b from the first communication hole 64 to thereby prevent water from being supplied to the lower side portion 5b. The communication groove 62 faces this time both of the upper and lower side portions 6a and 6b of the water supply passage 6 to communicate these portions 6a and 6b with each other. Cleaning liquid (or water) is thus fed from the water supply tank 14 to the nozzle 7 through the water supply passage 6 to be jetted out of the nozzle 7.

As shown in FIG. 2, the control valve 21 comprises a cylinder 71 and a piston 72, and the cylinder 71 is of bottomed cylindrical shape whose one end is opened. The opened end of the cylinder 71 is fixedly fitted into a hole 73 formed in the wall 5 of the operating section 3. An opening 74 to which the lower side portion of the suction passage 17 is connected is formed in the bottom wall of the cylinder 71. A flange 77 for closing an urging member 76 which will be described later is formed projecting from the outer end of the cylinder 71. This flange 77 has a shape similar to that of the flange 39 in the case of the control valve 22 and allows the urging member 76 to be freely detachably attached thereto. The urging member 76 also has an arrangement similar to that of the urging member 41 in the case of the control valve 22, and the lower end of the urging member 76 is elastically and sealingly fitted onto the flange 77 while the upper end thereof is freely detachably and elastically attached to a stopper ring 78 formed at the upper end of the piston 72. A hole 79 is formed inside the the piston 72 along the axis thereof and communicates with a communication hole 81 which is formed halfway of the side wall of the piston 72. The communication hole 81 is located above the outer end of the cylinder 71 when the piston 72 is kept ready for operation as shown in FIG. 2. When the piston 72 is pushed, the communication hole 81 is moved into correspondence with an opening 75 to communicate therewith. A leak hole 82 is formed inside the piston 72 along the axis thereof and at the outer end thereof. The leak hole 82 is opened outside and communicates with a side hole 83 formed halfway of the side wall of the piston 72.

When the piston 72 is kept ready for operation as shown in FIG. 2, the opening 75 in the control valve 21 is closed by the outer circumference of the piston 72 to shield the suction passage 17. When suction is to be performed, a finger is put on the outer end of the piston 72 to close the leak hole 82 and to push the piston 72 into the cylinder 71 against the urging member 76. The communication hole 81 of the piston 72 thus comes to face the opening 75 to communicate therewith. The suction passage 17 is thus communicated to perform suction through the tool inserting channel 18.

Figure 3:
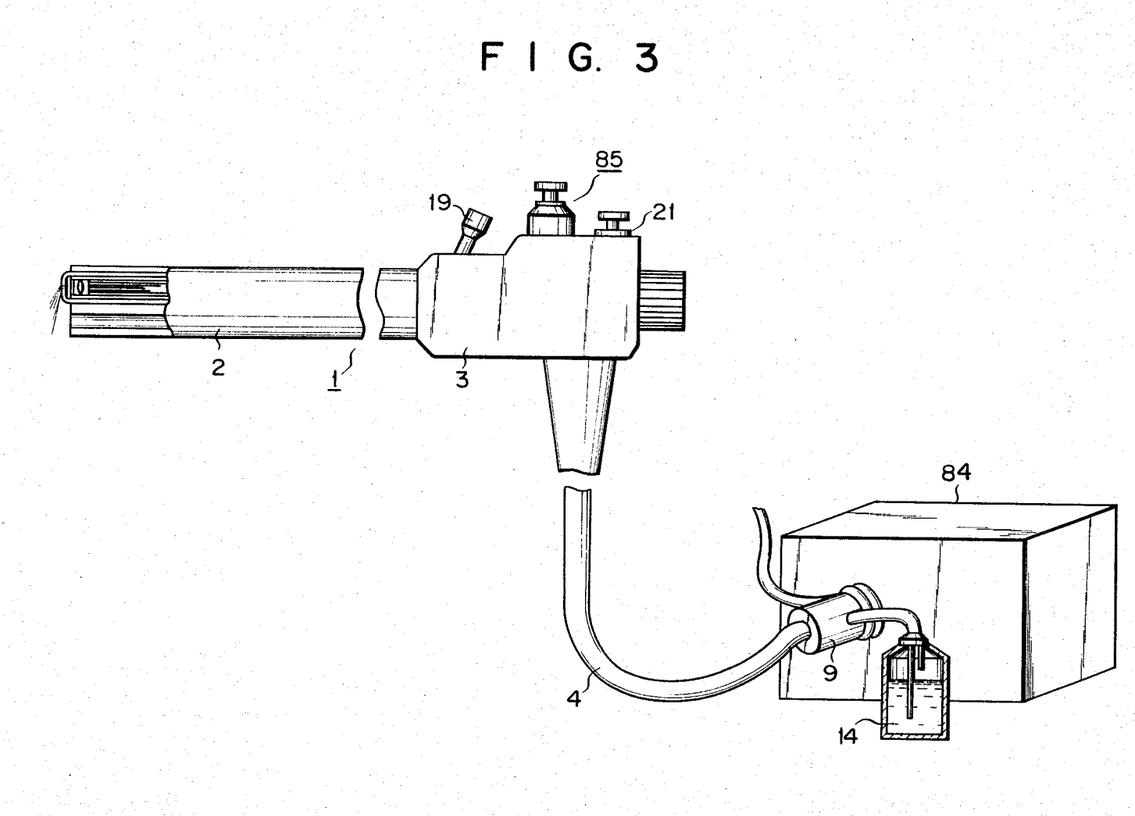
FIG. 3 is a side view showing the first embodiment of the present invention used.

The pistons 31 and 72 in both of the control valves 21 and 22 can be detached from the cylinders 30 and 71 together with the urging members 41 and 76, when the urging members 41 and 76 are removed from the flanges 39 and 77 of the cylinders 30 and 71. Numeral 84 in FIG. 3 represents a light source means to which the connector 9 is connected.

A device for cleaning passages in the endoscope 1 which has such arrangement as described above will be described referring to FIGS. 3 through 5.

Figure 4:
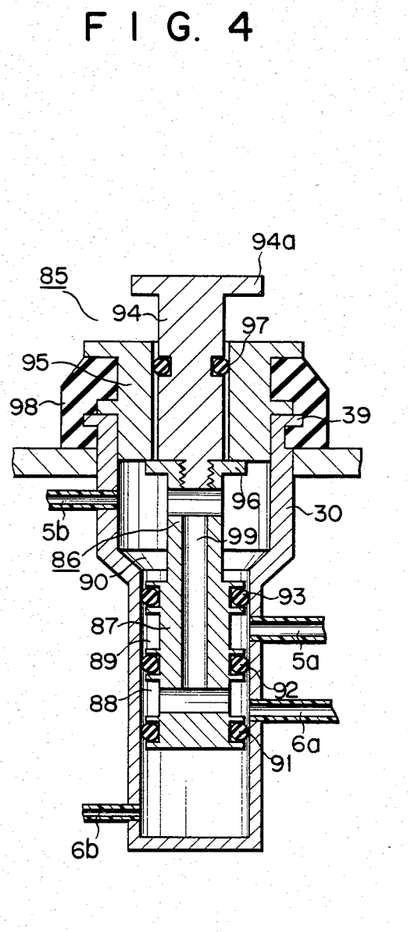
FIGS. 4 and 5 are sectional views showing a part of the first embodiment under different states.
Figure 5:
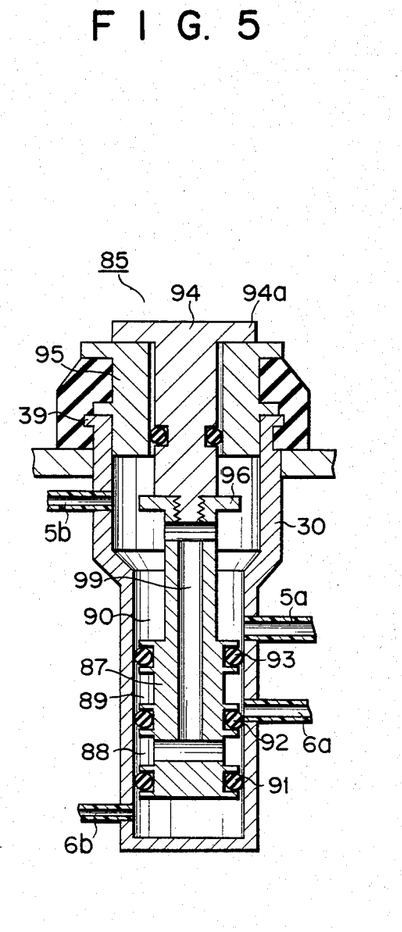

The cleaning device 85 has a communication member 86 which is inserted into the cylinder 30 of the control valve 22 after the piston 31 is removed from the cylinder 30. First, second and third ring-shaped communication grooves 88, 89 and 90 are formed around the outer circumference of an inserted end 87 of the communication member 86 with a predetermined distance interposed between the adjacent communication grooves in the axial direction of the communication member 86. O-rings 91, 92 and 93 are located on the outer circumference of the inserted end 87 at the backs and fronts of the first and second communication grooves 88 and 89 to slide on the inner face of the cylinder 30 to thereby prevent leaking from the communication grooves 88, 89 and 90. The communication member 86 has a cylindrical push button 94 screwed into the outer end of the inserted end portion 87, and the push button 94 is inserted into a housing member 95 with its outer end projected outside. The push button 94 is provided with a collar 94a formed integral at the outermost end thereof. The inserted end portion 87 is also provided with a collar 96 formed integral at the outermost end thereof. As shown in FIGS. 4 and 5, the push button 94 can reciprocate from a position where the collar 96 hits the housing member 95 to another position where its collar 94a hits the housing member 95. An O-ring 97 is fitted around the outer circumference of the push botton 94 to slide on the inner face of the housing member 95 to thereby prevent leaking between the outer circumference of the push button 94 and the inner face of the housing member 95. The housing member 95 is freely detachably engaged with the flange 39 of the fitting 34 located at the outer end of the cylinder 30 by means of an elastic engaging member 98.

A communication hole 99 is formed inside the inserted end portion 87 of the communication member 86 along the axial direction thereof, and one end of this communication hole 99 is communicated with the first communication groove 88 through a traverse hole while the other end thereof is communicated with the third communication groove 90 through a traverse hole.

When the push button 94 is drawn under this state to lift the communication member 86, the first communication groove 88 is communicated with the upper side portion 6a of the water supply passage 6, the second communication groove 89 with the upper side portion 5a of the air supply passage 5, and the third communication groove 90 with the lower side portion 5b of the air supply passage 5, as shown in FIG. 4. When the push button 94 is pushed to lower the communication member 86 as shown in FIG. 5, the upper and lower side portions 5a and 5b of the air supply passage 5 are communicated with each other through the third communication groove 90 and also communicated with the first communication groove 88. More specifically, when the push button 94 is in the lifted position, the air supply passage 5 is shut off while the upper side portion 6a of the water supply passage 6 is communicated with the lower side portion 5b of the air supply passage 5 through the first communication groove 88, communication hole 99 and third communication groove 90. When the push button 94 is in the pushed position, the water supply passage 6 is shut off while the upper and lower side portions 5a and 5b of the air supply passage 5 are communicated with each other through the third communication groove 90. The communication member 86 serves to selectively change over the two positions as described above.

Using the cleaning device 85, it will be described how each of the passages 5, 6 and 17 in the endoscope 1 is cleaned.

After use of the endoscope 1, dirt on its insert section 2 is cleanly wiped out by using sterilizating alcohol. The inside of the water supply passage 6 is cleaned by feeding water therethrough. The inside of the suction passage 17 is also cleaned by repeating suction therethrough with the insert section 2 of the endoscope 1 immersed in cleaning liquid.

The communication member 86 is inserted into the cylinder 30 for the air and water supply control valve 22 as shown in FIG. 4, after the piston 31 is removed from the cylinder 30. The push button 94 is then lifted to allow enough water to be fed from the upper side portion 6a of the water supply passage 6 to the lower side portion 5b of the air supply passage 5. Thereafter, the push button 94 is pushed down as shown in FIG. 5, and the water supply passage is thus shut off while the air supply passage 5 is communicated to allow air to be supplied therethrough, whereby drying inside the air supply passage 5 can be attained completely. After these serial processes, the communication member 86 is removed while the piston 31 is inserted into the cylinder 30. Cleaning of the passages line and the insert section 2 is thus finished.

Figure 6:
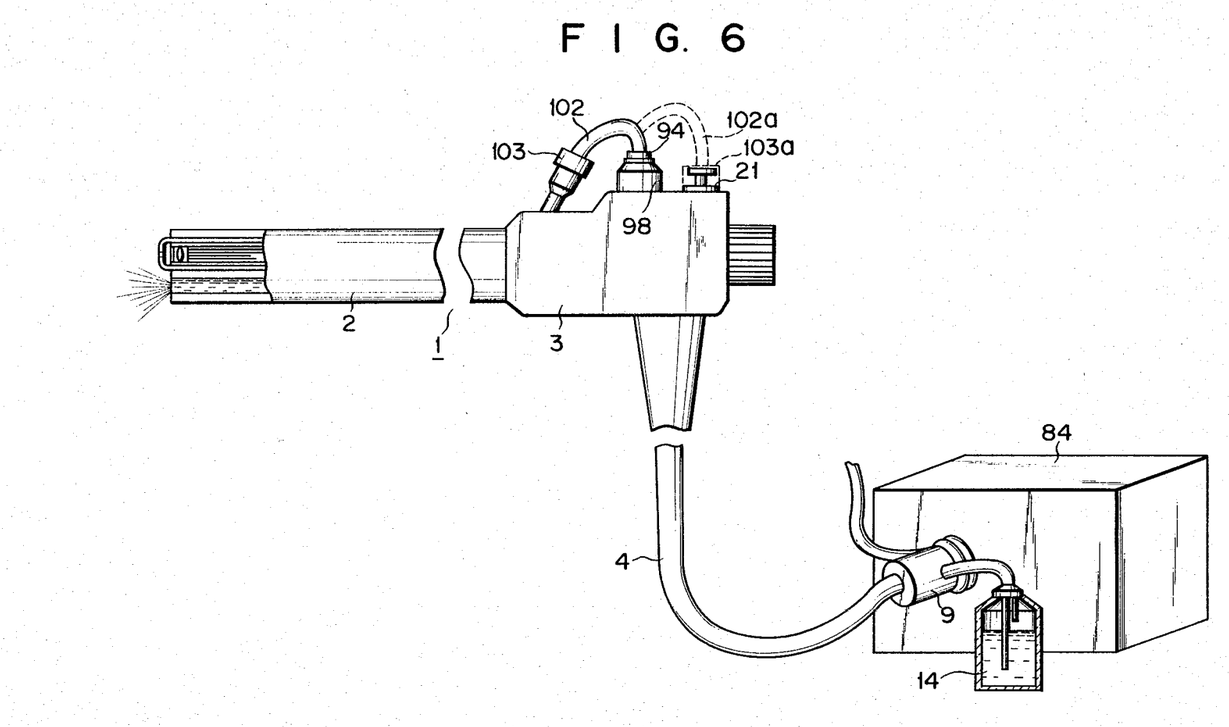
FIG. 6 is a side view showing a second embodiment of cleaning device according to the present invention.
Figure 7:
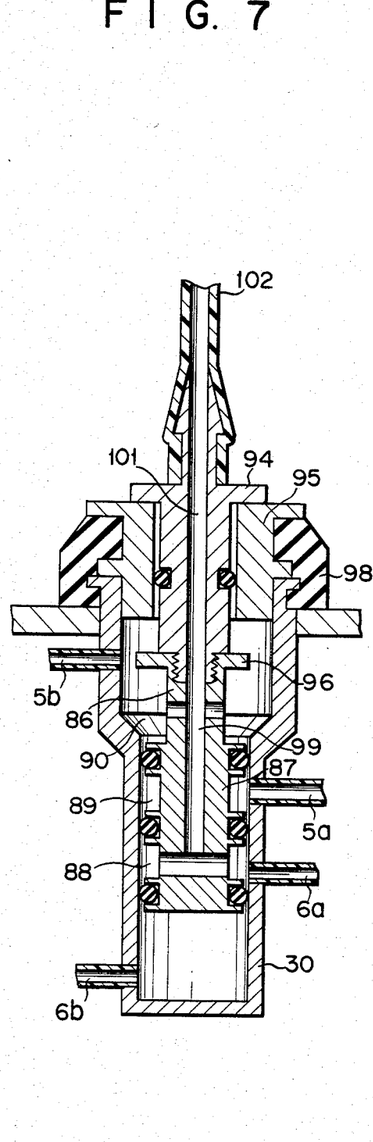
FIGS. 7 and 8 are, respectively, sectional views showing a part of the cleaning device under different states.
Figure 8:
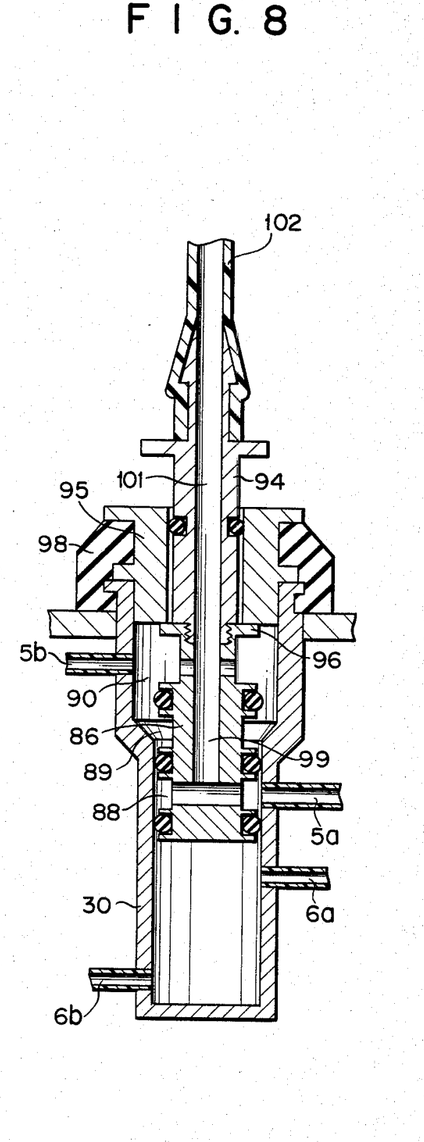

A second embodiment of cleaning device according to the present invention will be described referring to FIGS. 6 through 8.

Same parts as those of the first embodiment will be represented by the same numerals and description of these parts will be omitted. A hole 101 which communicates with the communication hole 99 is formed extending through the inserted end portion 87 of the communication member 86 and the push button 94, and a tube 102 which communicates with the hole 101 is connected to the outer end of the push button 94. A suction passage connecting member 103 which can be engaged with both of the forceps opening 19 and the cylinder 71 for suction control valve 21, that is, the flange 77 thereof is attached to the extended front end of the tube 102. Alternately, another suction passage connecting member 103a may be provided at one end of a branched tube 102a of the main tube 102 as shown by dash line in FIG. 6.

When cleaning is to be achieved by the second embodiment of cleaning device having such arrangement as described above, the suction passage connecting member or members 103 are water-tightly engaged with the forceps opening 19 and/or the opened end of the cylinder 71 from which the piston has been removed. When the push button 94 is then pushed as shown in FIG. 7, water is supplied into the whole of the suction passage 17 through the hole 101 and the tube 102 as well as into the lower side portion 5b of the air supply passage 5, so that both of the air supply passage 5 and the suction passage 17 can be cleaned. When the push button 94 is lifted as shown in FIG. 8, drying can be achieved both in the lower side portion 5b of the air supply passage 5 and in the suction passage 17.

Although the communication member 86 has been moved up and down by the push button 94 to change over the passages in the case of the above-described embodiments, changeover of the passages may be attained by a communication member which is made to have double cylinders. Namely, these double cylinders of the communication member may be appropriately rotated relative to each other to change over the passages in the endoscope.

As described above, the cleaning device according to the present invention enables the passages in the endoscope to be easily cleaned without changing the design of the air and water supply mechanism conventionally employed in the endoscope, without connecting and removing a variety of tubes, and also without detaching the endoscope from the light source means, pumps and the like. Further, no specified means such as the exclusive pump is needed. Furthermore, water can be supplied to the air supply nozzle to solve jamming of the nozzle.

When the cleaning device is provided with the changeover mechanism, drying after cleaning can be easily achieved. In addition, even the suction passage can be fully cleaned by water supplied, so that dirt and the like in the suction passage are drawn neither into the suction cylinder nor further inside.

What is claimed is:

1. A device for cleaning an endoscope comprising an insert section which is inserted into a body cavity from a front end thereof; an operation section connected to a base end of the insert section; an air and water supply cylinder arranged in the operation section; a changeover piston slidable in the cylinder and detachable from the cylinder; an air supply passage having a lower side portion, one end of which is opened at the front end of the insert section while the other end thereof is communicated with the cylinder, and an upper side portion, one end of which is communicated with the cylinder while the other end thereof is connected to a means for supplying air; a water supply passage having a lower side portion, one end of which is opened at the front end of the insert section while the other end thereof is communicated with the cylinder, and an upper side portion, one end of which is communicated with the cylinder while the other end thereof is connected to a means for supplying water; an instrument inserting channel; a suction cylinder arranged in the operation section; a changeover piston slidable in the suction cylinder and detachable from the suction cylinder; and a suction passage having an upper side portion, one end of which is opened at the front end of the insert section, said suction passage being connected halfway thereof to the instrument inserting channel, and the other end of the suction passage being communicated with the suction cylinder, and said suction passage having a lower side portion, one end of which is communicated with the suction cylinder while the other end thereof being connected to a means for producing suction; said device comprising
   a communication member inserted into the air and water supply cylinder after removing the changeover piston from the cylinder to communicate at least one of the combinations consisting of the upper side portion of the water supply passage and the lower side portion of the air supply passage, and consisting of the upper side portion of the water supply passage and the suction passage;
   said communication member being inserted to move in the air and water supply cylinder between first and second positions and having a changeover mechanism which allows the upper side portion of the water supply passage to be communicated with the lower side portion of the air supply passage when said communication member is in the first position; and said changeover mechanism allows the upper side portion of the air supply passage to be communicated with the lower side portion of the air supply passage when said communication member is in the second position.

2. A device according to claim 1 wherein the changeover mechanism allows the upper side portion of the water supply passage to be communicated with the lower side portion of the air supply passage while at least one of the instrument inserting channel and the suction cylinder to be communicated therewith when said communication member is in the first position; and said changeover mechanism allows the upper side portion of the air supply passage to be communicated with the lower side portion thereof when said communication member is in the second position.

3. A device according to claim 2 wherein said changeover mechanism allows the upper side portion of the water supply passage to be communicated with the lower side portion of the air supply passage while at least one of the instrument inserting channel and the suction cylinder to be communicated therewith when said communication member is in the second position.

4. A device for cleaning an endoscope comprising an insert section which is inserted into a body cavity from a front end thereof; an operation section connected to a base end of the insert section; and air and water supply cylinder arranged in the operation section; a changeover piston slidable in the cylinder and detachable from the cylinder; and air supply passage having a lower side portion, one end of which is opened at the front end of the insert section while the other end thereof is communicated with the cylinder, and an upper side portion, one end of which is communicated with the cylinder while the other end thereof is connected to a means for supplying air; and a water supply passage having a lower side portion, one end of which is opened at the front end of the insert section while the other end thereof is communicated with the cylinder, and an upper side portion, one end of which is communicated with the cylinder while the other end thereof is connected to a means for supplying water;

said device comprising a communication member inserted into the air and water supply cylinder after removing the changeover piston from the cylinder to communicate the upper side portion of the water supply passage and the lower side portion of the air supply passage, said communication member being inserted to move in the air and water supply cylinder between first and second positions and having a changeover mechanism which allows the upper side portion of the water supply passage to be communicated with the lower side portion of the air supply passage when said communication member is in the first position; and said changeover mechanism allows the upper side portion of the air supply passage to be communicated with the lower side portion of the air supply passage when said communication member is in the second position.

5. A device according to claim 4 wherein said communication member is of a piston shape slidably insertable into the air and water supply cylinder, and said changeover mechanism has an opening communicated with the lower side portion of the air supply passage and an opening communicated with the upper side portion of the water supply passage when said communication member is in the first position, and said changeover mechanism also has a through-hole formed through the communication member.

6. A device according to claim 5 further including a housing member for supporting the communication member slidably and closing the air and water supply cylinder.

* * * * *